(12) United States Patent
Morino et al.

(10) Patent No.: US 11,408,868 B2
(45) Date of Patent: Aug. 9, 2022

(54) MEASURING SYSTEM AND MEASURING METHOD OF HYDROGEN PEROXIDE CONCENTRATION

(71) Applicant: ORGANO CORPORATION, Tokyo (JP)

(72) Inventors: Shota Morino, Tokyo (JP); Daisaku Yano, Tokyo (JP); Yukinari Yamashita, Tokyo (JP); Masayuki Kawakami, Tokyo (JP)

(73) Assignee: ORGANO CORPORATION, Tokyo (JP)

( * ) Notice: Subject to any disclaimer, the term of this patent is extended or adjusted under 35 U.S.C. 154(b) by 0 days.

(21) Appl. No.: 16/966,631

(22) PCT Filed: Sep. 12, 2018

(86) PCT No.: PCT/JP2018/033760
§ 371 (c)(1),
(2) Date: Jul. 31, 2020

(87) PCT Pub. No.: WO2019/150640
PCT Pub. Date: Aug. 8, 2019

(65) Prior Publication Data
US 2021/0033581 A1 Feb. 4, 2021

(30) Foreign Application Priority Data

Jan. 31, 2018 (JP) ............................. JP2018-014416

(51) Int. Cl.
*G01N 31/22* (2006.01)
*G01N 33/18* (2006.01)
(52) U.S. Cl.
CPC ............ *G01N 31/228* (2013.01); *G01N 33/18* (2013.01); *Y10T 436/206664* (2015.01); *Y10T 436/209163* (2015.01)

(58) Field of Classification Search
CPC ...... G01N 31/00; G01N 31/228; G01N 33/18; Y10T 436/20; Y10T 436/206664; Y10T 436/207497; Y10T 436/209163
(Continued)

(56) References Cited

U.S. PATENT DOCUMENTS

2007/0238188 A1 10/2007 Carr
2021/0181167 A1* 6/2021 Sundstrom ................ C02F 1/42

FOREIGN PATENT DOCUMENTS

JP 55143437 * 11/1980
JP 10-96720 A 4/1998
(Continued)

OTHER PUBLICATIONS

International Search Report issued in International Patent Application No. PCT/JP2018/033760, dated Dec. 11, 2018, and English Translation thereof.
(Continued)

*Primary Examiner* — Maureen Wallenhorst
(74) *Attorney, Agent, or Firm* — Greenblum & Bernstein, P.L.C.

(57) ABSTRACT

Provided are a method and system for measuring hydrogen peroxide concentration in sample water collected from a prescribed position in a water treatment process and includes: collecting the sample water; measuring a concentration of a dissolved oxygen in the sample water or a treated water obtained by treating the sample water with the hydrogen peroxide decomposing device by first and second dissolved oxygen concentration measuring analyzers to obtain a corrected value that is a difference between the two dissolved oxygen concentration values; measuring the concentration of the dissolved oxygen in the sample and treated water by the first and second dissolved oxygen concentration measuring analyzers, respectively, and obtaining a measured
(Continued)

value that is a difference between the dissolved oxygen concentration values; and calculating a corrected concentration of hydrogen peroxide from the measured value obtained during the measured value obtaining and the corrected value obtained during the corrected value obtaining.

10 Claims, 5 Drawing Sheets

(58) Field of Classification Search
USPC ................................. 436/127, 135, 136, 138
See application file for complete search history.

(56) References Cited

FOREIGN PATENT DOCUMENTS

| JP | 2005-274386 A | 10/2005 |
| JP | 2012-63303 A | 3/2012 |
| JP | 2012061443 | * 3/2012 |
| JP | 2012063303 | * 3/2012 |
| JP | 2013-108916 A | 6/2013 |
| JP | 2017-000970 A | 1/2017 |
| JP | 2018025454 | * 2/2018 |
| WO | 2018/017672 | 1/2018 |

OTHER PUBLICATIONS

Office Action issued in corresponding Indian Patent Application No. 202047036355 dated Jul. 12, 2921, along with English translation thereof.

* cited by examiner

Prior Art

MEASURING SYSTEM AND MEASURING METHOD OF HYDROGEN PEROXIDE CONCENTRATION

TECHNICAL FIELD

The present invention relates to a measuring system and a measuring method for measuring a concentration of trace hydrogen peroxide in a sample water.

BACKGROUND ART

As a method for analyzing the concentration of hydrogen peroxide, a method using a test paper or a test reagent, a colorimetric method, an oxidation-reduction titration method, and the like are generally known. Such a concentration analysis of hydrogen peroxide is used for various purposes, and can be used, for example, in a wastewater treatment facility for wastewater containing hydrogen peroxide. It is also known that hydrogen peroxide is generated in ultraviolet irradiation equipment or the like in a pure water or ultrapure water production facility, and the necessity of analyzing the concentration of hydrogen peroxide is being recognized. In order to analyze the concentration of hydrogen peroxide in the pure water or ultrapure water production facility, a microanalysis with an analytical value of the µg/L level is required. Among the various analytical methods described above, the analytical values of µg/L levels are difficult to measure using test paper or test reagents.

In addition, the colorimetric method and the oxidation-reduction titration method are complicated in colorimetric analysis and titration operations, difficult to perform in-pipe line automatic analysis, and are unsuitable for the pure water or ultrapure water production facilities that desire to eliminate human intervention as much as possible. In addition, the need for reagents increases driving costs due to chemical costs, maintenance, post-analysis waste disposal, and the like.

In view of the above problems, Patent Document 1 discloses a hydrogen peroxide analyzer and a hydrogen peroxide analysis method that can easily and sensitively analyze a micro amount of hydrogen peroxide in water. The invention disclosed in Patent Document 1 is a method of calculating a concentration of hydrogen peroxide in a sample water by a hydrogen peroxide decomposing means and one or two dissolved oxygen concentration analyzers. Specifically, the concentration of hydrogen peroxide in the sample water is calculated from the difference between the concentration of dissolved oxygen in the sample water and the concentration of dissolved oxygen in the treated water treated by the hydrogen peroxide decomposition means. An example of the configuration of an embodiment of the apparatus is shown in FIG. 8 (corresponding to FIG. 6 of Patent Document 1) and FIG. 9 (corresponding to FIG. 3 of Patent Document 1). In FIG. 8, the dissolved oxygen concentrations contained in the sample water and the treated water are measured alternately by one dissolved oxygen analyzer. In FIG. 9, the dissolved oxygen concentrations contained in the sample water and the treated water are measured simultaneously by two dissolved oxygen analyzers.

Patent Document 2 also discloses an apparatus and a method for measuring a concentration of hydrogen peroxide, wherein a catalytic metal carrier in which a platinum group metal is supported on a monolithic organic porous anion exchanger is used as the hydrogen peroxide decomposing means. Patent Document 3 discloses a method for measuring a concentration of hydrogen peroxide by a phenolphthalein colorimetric method using a solid coloring reagent.

PRIOR ART LITERATURE

Patent Documents

Patent Document 1: JP2005-274386A
Patent Document 2: JP2012-63303A
Patent Document 3: JPH10-96720A

SUMMARY OF INVENTION

Problems to be Solved by Invention

In the configuration of FIG. 8 in which there is one dissolved oxygen analyzer, since the concentrations of dissolved oxygen contained in the sample water and the treated water subjected to the decomposition treatment of hydrogen peroxide are alternately measured, and then the concentration of hydrogen peroxide is calculated from the difference between the concentrations of dissolved oxygen in the sample water and the treated water, the concentration of hydrogen peroxide in the sample water cannot be measured frequently. In addition, the dissolved oxygen concentration in the sample water cannot be measured while the dissolved oxygen concentration in the treated water is measured. Further, by switching between the sample water and the treated water, it takes some time to stabilize the measured value of dissolved oxygen concentration after the switching.

In the configuration of FIG. 9 in which the dissolved oxygen analyzer is increased to two units, the concentration of hydrogen peroxide is calculated from the difference between the dissolved oxygen concentrations of the sample water and the treated water subjected to the decomposition treatment of hydrogen peroxide while simultaneously measuring the dissolved oxygen concentrations of the sample water and the treated water. Therefore, the concentration of hydrogen peroxide can be calculated continuously. In addition, the dissolved oxygen concentration in the sample water can also be measured continuously. However, slight individual differences between the two dissolved oxygen analyzers can lead to errors in a measurement of the concentration of hydrogen peroxide.

In view of the above, it is an object of the present invention to provide a method and a measurement system for measuring a hydrogen peroxide concentration capable of continuously and accurately quantifying hydrogen peroxide in a sample water.

Means for Solving the Problem

In order to solve the above problems, a method for measuring a concentration of hydrogen peroxide according to the present invention is a method for measuring the concentration of hydrogen peroxide in sample water collected from a predetermined position in a water treatment process, the method includes:

a collection step for collecting the sample water, a corrected value obtaining step for obtaining a corrected value that is a difference between two dissolved oxygen concentration values, the two dissolved oxygen concentration values in this step being measured by using a first dissolved oxygen concentration measuring means and a second dissolved oxygen concentration measuring means, respectively, for the sample water or a treated water obtained by treating the sample water with a hydrogen peroxide decomposing means, a measured value obtaining step for obtaining a measured value that is a difference between two dissolved oxygen concentration values, the two dissolved oxygen concentration values in this step being obtained by measuring a concentration of the dissolved oxygen in the sample water by the first dissolved oxygen concentration measuring means, and measuring a concentration of the dissolved oxygen in the treated water by the second dissolved oxygen concentration measuring means, and a calculation step for calculating a corrected concentration of hydrogen peroxide from the measured value obtained in the measured value obtaining step and the corrected value obtained in the corrected value obtaining step.

In addition, a measurement system of hydrogen peroxide concentration according to the present invention is a hydrogen peroxide concentration measurement system for measuring the concentration of hydrogen peroxide in sample water collected from a predetermined position in a water treatment process, the system includes:

a sample water collecting means collecting the sample water, a route introducing the sample water into a first dissolved oxygen concentration measuring means through a first pipe line to measure a concentration of dissolved oxygen, a route introducing the collected sample water into a hydrogen peroxide decomposition means to obtain a treated water subjected to a decomposition treatment of the hydrogen peroxide, and introducing the treated water into a second dissolved oxygen concentration measuring means through a second pipe line to measure the dissolved oxygen concentration in the treated water, a connection pipe line connecting the first pipe line and the second pipe line, a first on-off valve disposed on the upstream side of the branch position in at least one of the first pipe line and the second pipe line with the connection pipe line, a connection valve disposed in the connection pipe line, a valve control means for controlling the opening and closing of the first on-off valve and the connection valve, a calculation means calculating a corrected concentration of hydrogen peroxide from a measured value that is a difference between the dissolved oxygen concentration value of the sample water measured by the first dissolved oxygen concentration measuring means and the dissolved oxygen concentration value of the treated water measured by the second dissolved oxygen concentration measuring means, and a correction value that is a difference between the dissolved oxygen concentration values of the sample water or the treated water measured by the first and second dissolved oxygen concentration measuring means.

Effects of the Invention

According to the present invention, it is possible to provide a method and a measurement system for measuring a hydrogen peroxide concentration capable of continuously and accurately quantifying hydrogen peroxide in sample water.

DESCRIPTION OF THE EMBODIMENTS

Hereinafter, embodiments of the present invention will be described with reference to the drawings. However, the present invention is not limited to the embodiments.

Figure 1:
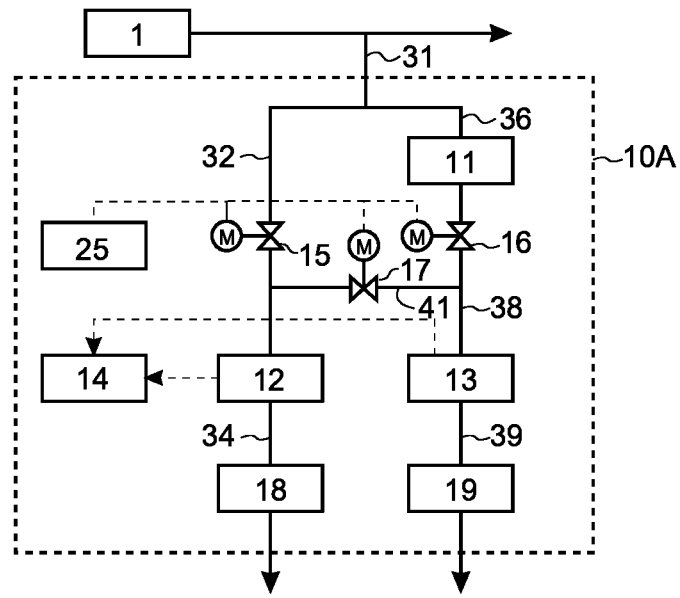
FIG. 1 is a configuration diagram of a hydrogen peroxide concentration measurement system according to an embodiment of the present invention.

FIG. 1 is a block diagram showing a configuration of a hydrogen peroxide concentration measurement system 10A according to an embodiment of the present invention. As shown in FIG. 1, the hydrogen peroxide concentration measurement system 10A collects sample water to be analyzed by a sample water collection pipe line (sample water collecting means) 31 from a predetermined position before or after processing in the water treatment process 1, such as a manufacturing facility of pure water or ultrapure water, a wastewater processing facility, or the like, and the collected sample water is introduced into the measurement system.

The sample water is branched into a route introducing the sample water into a first dissolved oxygen analyzer (first dissolved oxygen concentration measuring means) 12 through a first pipe line 32 to measure a concentration of dissolved oxygen, and a pipe line 36 connected to a route introducing the sample water into a hydrogen peroxide decomposition device (hydrogen peroxide decomposition means) 11 to obtain a treated water subjected to a decomposition treatment of the hydrogen peroxide and introducing the treated water into the second dissolved oxygen analyzer (second dissolved oxygen concentration measuring means) 13 through a second pipe line 38 to measure the dissolved oxygen concentration.

That is, the first dissolved oxygen analyzer 12 receives the sample water as it is and measures the dissolved oxygen concentration in the sample water. The hydrogen peroxide decomposition device 11 receives the sample water, decomposes the hydrogen peroxide in the sample water, and discharges it as treated water. The second dissolved oxygen analyzer receives the discharged treated water and measures the dissolved oxygen concentration in the treated water.

As shown in FIG. 1, the sample water collection pipe line 31 branches and is divided into two measurement lines (two routes). The sample water flowing into the first pipe lines 32 that is one of the branches is sent to the first dissolved oxygen analyzer 12 via the first on-off valve 15. The sample water flowing into the other pipe line 36 passes through the hydrogen peroxide decomposition device 11 and undergoes decomposition treatment of hydrogen peroxide. The treated water is sent to the second dissolved oxygen analyzer 13 via the second pipe line 38 having the second on-off valve 16. A connection pipe line 41 is provided to connect the downstream side of the first on-off valve 15 of the pipe line 32 to the downstream side of the second on-off valve 16 of the pipe line 38. A connection valve 17 is provided in the connection pipe line 41. The sample water collection pipe line 31 may be provided with a partition valve used when sample water is not collected. Note that the obtained sample water flows under the back pressure from the water treatment process 1, and therefore, a liquid feeding device such as a pump is unnecessary, but the liquid feeding device may be provided as needed.

Each of the first on-off valve 15, the second on-off valve 16, and the connection valve 17 is an automatic on-off valve operated by electricity, compressed air, or the like, and is controlled to open and close by a valve control device (valve control means) 25 including the timing of opening and closing. The values of the dissolved oxygen concentration measured by the first dissolved oxygen analyzer 12 and the second dissolved oxygen analyzer 13 are transmitted to an arithmetic unit (calculation means) 14, and the concentration of hydrogen peroxide in the sample water is calculated. A display device for displaying the measured dissolved oxygen concentration value and the calculated hydrogen peroxide concentration value on a monitor screen or the like in real time, or an output device for printing on a printer or the like as appropriate may be provided (they are not shown).

The hydrogen peroxide contained in the sample water introduced into the hydrogen peroxide decomposition device 11 is decomposed as follows. The generated oxygen dissolves in water and becomes dissolved oxygen.

$$2H_2O_2 \rightarrow 2H_2O + O_2 \quad (1)$$

The hydrogen peroxide decomposition device 11 may be constituted by a vessel or column filled with a material having a hydrogen peroxide decomposability. The material having the hydrogen peroxide decomposability may be any material as long as it has the ability to decompose hydrogen peroxide in water into water and oxygen, and is not particularly limited, but it is preferable that it is not dissolved by water, has a high hydrogen peroxide decomposability, and is excellent in durability. In order to improve the contact efficiency with hydrogen peroxide, a material having a large surface area, such as granular, fibrous, or porous, is preferable. Examples of such materials include activated carbon, synthetic carbon-based adsorbents, ion exchange resins, metal catalysts (Pd, Pt, etc.), enzymes (catalase, etc.), and enzyme carriers.

As a hydrogen peroxide decomposition catalyst, it is preferable to use a catalyst metal support (platinum group metal catalyst) on which a platinum group metal is supported. Hydrogen peroxide in the water to be treated is contacted with a platinum group metal catalyst, and hydrogen peroxide can be decomposed by catalytic decomposition. The platinum group metal catalyst is supported, for example, on an anion exchanger. The anion exchanger may be a granular anion exchange resin. Furthermore, it is preferable to use a platinum group metal catalyst having a platinum group metal supported on a monolithic organic porous anion exchanger in which an anion exchange resin is integrally formed for the following reasons.

A catalyst metal support in which a platinum group metal is supported on a monolithic organic porous anion exchanger can decompose hydrogen peroxide even if water is passed through the catalyst metal support at an SV (space velocity) exceeding 2,000 $h^{-1}$. This facilitates miniaturization of the hydrogen peroxide decomposition device 11. Moreover, the synergistic effect of the increase of the SV and the miniaturization of the hydrogen peroxide decomposition means makes it possible to carry water at high speed. For this reason, oxygen remaining in the catalyst itself or in the packed column easily escapes, thereby improving the start-up speed of the system and enabling rapid measurement. Even in the case where oxygen is invaded through the joint, since oxygen is easily removed by increasing the SV, the adverse influence on the measurement accuracy is also suppressed.

In particular, a Pd monolith in which Pd as a platinum group metal is supported on a monolithic organic porous anion exchanger can allow water to be measured to flow at high speed, so that the device can be easily miniaturized. Further, since the SV is large, for example, even when air is invaded from a pipe line on the upstream side of the hydrogen peroxide decomposition device, an influence thereof can be suppressed. For example, when air is intermittently invaded, because of the high SV, the air is immediately pushed to the downstream side and does not stay in the hydrogen peroxide decomposition device for a long time. Even if air is continuously invaded, the air is diluted because of the large SV, and the influence on the measured value is mitigated. For this reason, it is possible to improve the analysis accuracy. When air remains in the catalyst itself or in the packed column at the start-up of the system, it is necessary to wait until the air escapes and the measured value is stabilized, but the remaining air is quickly removed because of the high SV, and the start-up time of the system is shortened.

Particularly preferred as monolithic anion exchangers are A-type and B-type as described below. The catalyst metal support in which the platinum group metal is supported on these monolithic anion exchangers can be suitably applied to the hydrogen peroxide decomposition device 11.

(A-Type Monolithic Anion Exchanger)

The A-type monolithic anion exchanger is obtained by introducing an anion exchange group into a monolith, and is a continuous macropore structure in which bubble-like macropores overlap with each other, and the overlapping portion becomes an opening (mesopore) having an average diameter of 30 to 300 µm, preferably 30 to 200 µm, particularly preferably 40 to 100 µm in a water-wetted state. The average diameter of the opening of the A-type monolithic anion exchanger is greater than the average diameter of the opening of the monolith because the entire monolith swells when introducing anion exchange groups into the monolith. When the average diameter of the opening in the water-wetted state is 30 µm or more, it is possible to easily prevent the pressure loss at the time of water passage from becoming large. When the average diameter of the opening in the water-wetted state is 300 µm or less, it is easy to secure contact between the water to be treated and the A-type monolithic anion exchanger and the supported nanoparticles of the platinum group metal. As a result, it is possible to easily prevent deterioration of the hydrogen peroxide decomposition property. Meanwhile, the average diameter of the opening of the monolith intermediate in the dry state, the average diameter of the opening of the monolith in the dry state, and the average diameter of the opening of the monolithic anion exchanger in the dry state mean values measured by the mercury press-in method. The average diameter of the opening of the A-type monolithic anion exchanger in the water-wetted state is a value calculated by multiplying the average diameter of the opening of the A-type monolithic anion exchanger in the dry state by the swelling rate. If the swelling rate of the A-type monolithic anion exchanger in the water-wetted state with respect to the average diameters of the openings of the dry monolith before and after the introduction of the anion exchange group is known, the average diameter of the opening of the A-type monolithic anion exchanger in the water-wetted state can be calculated by multiplying the swelling rate to the average diameter of the opening of the dry monolith.

In the A-type monolithic anion exchanger, the area of the framework portion appearing in the cross section in the SEM image of the cut surface of the continuous macropore structure is 25 to 50%, preferably 25 to 45%, in the image region. When the area of the framework portion appearing in the cross section is 25% or more in the image region, it is possible to easily prevent a thin framework from being formed and the mechanical strength from being lowered, and in particular, it is possible to easily prevent the monolithic anion exchanger from being largely deformed when water is passed at a high flow rate. Further, it is possible to easily prevent a reduction in the catalytic effect due to a reduction in the contact efficiency between the water to be treated and the A-type monolithic anion exchanger and the platinum group metal nanoparticles supported on the monolithic anion exchanger. If the area is 50% or less, it is possible to easily prevent the framework from becoming thick and the pressure loss at the time of water passage from increasing.

The total pore volume of the A-type monolithic anion exchanger is 0.5 to 5 ml/g, preferably 0.8 to 4 ml/g. When the total pore volume is 0.5 ml/g or more, it is possible to easily prevent the pressure loss at the time of water flow from increasing, and further, it is possible to easily prevent the amount of permeated fluid per unit cross-sectional area from decreasing and the throughput from decreasing. In the meantime, when the total pore volume is 5 ml/g or less, it is possible to easily prevent the mechanical strength from being lowered, and in particular, it is possible to easily prevent the A-type monolithic anion exchanger from being largely deformed when water is fed at a high flow rate. Furthermore, it is possible to easily prevent a reduction in the contact efficiency between the water to be treated and the A-type monolithic anion exchanger and the platinum group metal nanoparticles supported on the monolithic anion exchanger, and it is possible to easily prevent a reduction in the catalytic effect. The total pore volume of a monolith (monolith intermediate, monolith, monolithic anion exchanger) means a value measured by a mercury press-in method. Also, the total pore volume of the monolith (monolith intermediate, monolith, monolithic anion exchanger) is the same in both dry and wet conditions.

The pressure loss at the time of permeation of water into the A-type monolithic anion exchanger is preferably in the range of 0.001 to 0.1 MPa/m·LV, particularly in the range of 0.005 to 0.05 MPa/m·LV, as indicated by the pressure loss (hereinafter referred to as the "differential pressure coefficient") at the time of permeation of water through columns 1-m packed with the A-type monolithic anion exchanger at the water-permeation pipe linear velocity (LV) of 1 m/h.

The A-type monolithic anion exchanger has an anion exchange capacity per volume in the water-wet state of 0.4 to 1.0 mg-equivalent/ml. When the anion exchange capacity per volume is 0.4 mg-equivalent/ml or more, the amount of the platinum group metal supported by nanoparticles per volume can be easily prevented from decreasing. In the meantime, when the anion exchange capacity per volume is 1.0 mg-equivalent/ml or less, it is possible to easily prevent an increase in pressure loss at the time of water flow. The anion exchange capacity per weight of the A-type monolithic anion exchanger is not particularly limited, but is 3.5 to 4.5 mg-equivalent/g because the anion exchange groups are uniformly introduced into the surface of the porous body and the inside of the framework.

In the A-type monolithic anion exchanger, the material constituting the framework of the continuous macropore structure is an organic polymer material having a crosslinked structure. The crosslinking density of the polymer material is not particularly limited, but it is preferable to contain 0.3 to 10 mol %, preferably 0.3 to 5 mol % of a crosslinked structural unit, based on all the constituent units constituting the polymer material. When the crosslinked structural unit is 0.3 mol % or more, it can be easily prevented that the mechanical strength is insufficient, while when the crosslinked structural unit is 10 mol % or less, it can be easily prevented that the introduction of the anion exchange group becomes difficult. The type of the polymer material is not particularly limited, and for example, an aromatic vinyl polymer such as polystyrene may be used. The polymer may be a polymer obtained by copolymerizing a single vinyl monomer and a crosslinking agent, a polymer obtained by polymerizing a plurality of vinyl monomers and a crosslinking agent, or a blend of two or more kinds of polymers. Among these organic polymer materials, crosslinked polymers of aromatic vinyl polymers are preferable from the viewpoints of ease of formation of a continuous macropore structure, ease of introduction of anion exchange groups and high mechanical strength, and stability against acid or alkali, and particularly, a styrene-divinylbenzene copolymer or a vinyl benzyl chloride-divinylbenzene copolymer is a preferable material.

Anion exchange groups of the A-type monolithic anion exchanger include quaternary ammonium groups such as a trimethyl-ammonium group, a triethyl-ammonium group, a tributyl-ammonium group, a dimethyl-hydroxyethyl-ammonium group, a dimethyl-hydroxypropyl-ammonium group, and a methyl-dihydroxyethyl-ammonium group.

The introduced anion exchange groups are uniformly distributed not only on the surface of the porous body but also inside the framework of the porous body. The term "the anion exchange groups are uniformly distributed" as used herein means that the distribution of the anion exchange groups is uniformly distributed on the surface and the inside of the framework at least on the order of µm. The distributed state of the anion exchange group can be relatively easily confirmed by ion-exchanging the counter anion with chloride ion, bromide ion, or the like, and then using EPMA. In addition, when the anion exchange groups are uniformly distributed not only on the surface of the monolith but also inside the framework of the porous body, the physical properties and chemical properties of the surface and the inside can be made uniform, so that the durability against swelling and shrinkage is improved.

The A-type monolithic anion exchanger swells greatly, for example, 1.4 to 1.9 times as much as a big-bone monolith because the anion exchange group is introduced into the big-bone monolith. Therefore, even if the opening diameter of the big-bone monolith is small, the opening diameter of the monolithic ion exchanger is generally increased at the above-mentioned magnification. Further, even if the opening diameter is increased by swelling, the total pore volume does not change. Therefore, the A-type monolithic ion exchanger has a big-bone framework and therefore has high mechanical strength despite the remarkably large opening diameter.

(B-Type Monolithic Anion Exchanger)

The B-type monolithic anion exchanger is a co-continuous structure consisting of a three-dimensionally continuous framework of aromatic vinyl polymer containing 0.3 to 5.0 mol % of cross-linked structural units in the total structural units into which the anion exchange groups have been introduced, with an average framework thickness of 1 to 60 μm in the water-wet state, and three-dimensionally continuous voids between the framework, with an average diameter of 10 to 100 μm in the water-wet state, with a total pore volume of 0.5 to 5 ml/g, an ion exchange capacity per volume in the water-wet state of 0.3 to 1.0 mg-equivalent/ ml, and anion exchange groups uniformly distributed in the porous ion exchanger.

The B-type monolithic anion exchanger is a co-continuous structure consisting of a three-dimensionally continuous framework with an average thickness of 1 to 60 μm, preferably 3 to 58 μm, in the water-wet state, into which the anion exchange groups have been introduced, and three-dimensionally continuous voids between the frameworks with an average diameter of 10 to 100 μm, preferably 15 to 90 μm, particularly preferably 20 to 80 μm in the water-wet state. That is, the co-continuous structure is a structure in which a continuous framework phase and a continuous vacancy phase are intertwined, and both are three-dimensionally continuous. Since the continuous pores have higher continuity of pores and are not biased in size as compared with conventional open-cell monoliths or particle aggregation monoliths, an extremely uniform adsorption behavior of ions can be achieved. In addition, it has high mechanical strength due to its thick framework.

The thickness of the framework and the diameter of the pores of the B-type monolithic anion exchanger are larger than the thickness of the framework and the diameter of the pores of a monolith because the entire monolith swells when the anion exchange groups are introduced into the monolith. Since the continuous pores have higher continuity of pores and are not biased in size as compared with the conventional open-cell type monolithic organic porous anion exchanger or particle aggregation type monolithic organic porous anion exchanger, extremely uniform anion adsorption behavior can be achieved. If the average diameter of three-dimensionally continuous pores is 10 μm or more in the water-wetted state, it is possible to easily prevent a large pressure loss at the time of water flow. If the average diameter is 100 μm or less, it is easy to secure contact between the water to be treated and the organic porous anion exchanger, and as a result, it is easy to remove dissolved oxygen in the water to be treated. Further, when the average thickness of the framework is 1 μm or more in the water-wetted state, it is possible to easily prevent the anion exchange capacity per volume from decreasing, and it is possible to easily prevent the mechanical strength from decreasing. In particular, the large deformation of the B-type monolithic anion exchanger when water is passed at a high flow rate can be easily prevented. Furthermore, it is possible to easily prevent a reduction in the catalytic effect due to a reduction in the contact efficiency between the water to be treated and the B-type monolithic anion exchanger. In the meantime, when the thickness of the framework is 60 μm or less, it is possible to easily prevent the framework from becoming thick and increasing the pressure loss at the time of water passage.

The average diameter of the pores of the continuous structure in the water-wetted state is a value calculated by multiplying the average diameter of the pores of the monolithic anion exchanger in the dry state measured by the mercury press-in method by the swelling rate. When the average diameter of the pores of the monolith in the dry state before the introduction of the anion exchange group and the swelling rate of the monolithic anion exchanger in the water-wetted state with respect to the monolith in the dry state when the anion exchange group is introduced into the monolith in the dry state are known, the average diameter of the pores of the monolithic anion exchanger in the water-wetted state can be calculated by multiplying the swelling rate to the average diameter of the pores of the monolith anion exchanger in the dry state. The average thickness of the framework of the continuous structure in the water-wetted state is a value obtained by the following procedures: performing SEM observations of the B-type monolithic anion exchanger in the dry state at least three times, measuring respective thicknesses of the framework in the obtained SEM images, and multiplying the average value of the measured thicknesses by the swelling rate. Further, when the average thickness of the framework of the monolith in the dry state before the introduction of the anion exchange group and the swelling rate of the B-type monolithic anion exchanger in the water-wetted state with respect to the monolith in the dry state when the anion exchange group is introduced into the monolith in the dry state are known, the average thickness of the framework of the B-type monolithic anion exchanger in the water-wetted state can be calculated by multiplying the swelling rate to the average thickness of the framework of the monolith in the dry state. The framework is rod-shaped and has a circular cross-sectional shape, but may include an elliptical cross-sectional shape or other cross-sectional shape having a different diameter. In this case, the thickness is an average of the minor axis and the major axis.

The total pore volume of the B-type monolithic anion exchanger is 0.5 to 5 ml/g. When the total pore volume is 0.5 ml/g or more, it is possible to easily prevent an increase in pressure loss during water flow, and further, it is possible to prevent a reduction in the amount of treated water due to a decrease in the amount of permeated water per unit cross-sectional area. In the meantime, when the total pore volume is 5 ml/g or less, it is possible to easily prevent a decrease in the anion exchange capacity per volume, and a decrease in the catalyst effect due to a decrease in the supported amount of the platinum group metal nanoparticles. In addition, it is possible to easily prevent a reduction in the mechanical strength, and particularly, the B-type monolithic anion exchanger from being deformed largely when water is passed at a high flow rate. Furthermore, it is possible to easily prevent the reduction of the hydrogen peroxide decomposition effect due to the reduction of the contact efficiency between the water to be treated and the B-type monolithic anion exchanger. If the three-dimensionally continuous pore size and the total pore volume are in the above range, the contact with the water to be treated is extremely uniform, the contact area is large, and water can be passed under the lower pressure loss. Note that the total pore volume of the monolith (monolith intermediate, monolith, monolithic anion exchanger) is the same in both dry and water wetted states.

The pressure loss when water is permeated through the B-type monolithic anion exchanger is, as indicated by the pressure loss (hereinafter referred to as the "differential pressure coefficient") when water is passed through the column in which the porous body is 1-m packed at the pipe line velocity (LV) of 1 m per hour, in the range of 0.001 to 0.5 MPa/m·LV, particularly in the range of 0.005 to 0.1 MPa/m·LV.

In the B-type monolithic anion exchangers, the material constituting the framework of the co-continuous structure is an aromatic vinyl polymer containing 0.3 to 5 mol %, preferably 0.5 to 3.0 mol %, of cross-linked structural units in the total structural units and is hydrophobic. When the crosslinked structural unit is 0.3 mol % or more, it is possible to easily prevent the mechanical strength from being insufficient, while when it is 5 mol % or less, it is possible to easily prevent the structure of the porous body from deviating from the co-continuous structure. The type of the aromatic vinyl polymer is not particularly limited and, for example, polystyrene can be exemplified. The polymer may be a polymer obtained by copolymerizing a single vinyl monomer and a crosslinking agent, a polymer obtained by polymerizing a plurality of vinyl monomers and a crosslinking agent, or a blend of two or more kinds of polymers. Among these organic polymer materials, styrene-divinylbenzene copolymers and vinylbenzyl chloride-divinylbenzene copolymers are preferable from the viewpoints of easy formation of a co-continuous structure, easy introduction of an anion exchange group, high mechanical strength, and high stability against acid or alkali.

The B-type monolithic anion exchanger has an ion exchange capacity of 0.3 to 1.0 mg-equivalent/ml as an anion exchange capacity per volume in the water-wetted state. Since the B-type monolithic anion exchanger has high continuity and uniformity of three-dimensionally continuous pores, even if the total pore volume is reduced, the pressure loss does not increase much. Therefore, it is possible to dramatically increase the anion exchange capacity per volume while keeping the pressure loss low. When the anion exchange capacity per volume is 0.3 mg-equivalent/ml or more, the supported amount of the nanoparticles of the platinum group metal per volume can be easily prevented from decreasing. In the meantime, when the anion exchange capacity per volume is 1.0 mg-equivalent/ml or less, it is possible to easily prevent an increase in pressure loss at the time of water penetration. The anion exchange capacity per weight of the B-type monolithic anion exchanger in the dry state is not particularly limited, but is 3.5 to 4.5 mg-equivalent/g because the ion exchange group is uniformly introduced to the framework surface and the inside of the framework of the porous body.

The anion exchange groups of the B-type monolithic anion exchanger may include those similar to those listed in the description of the A-type monolithic anion exchangers. Further, the distribution state of the anion exchange group, the meaning of "the anion exchange group is uniformly distributed", the confirmation method of the anion exchange group distribution state, and the effect that the anion exchange group is uniformly distributed not only on the surface of the monolith but also inside the framework of the porous body are the same as those of the A-type monolith anion exchanger.

The type of the polymer material of the monolithic intermediate is the same as the type of the polymer material of the monolithic intermediate of the A-type monolithic anion exchanger, and a description thereof is omitted.

The total pore volume of the monolithic intermediate is greater than 16 ml/g and 30 ml/g or less, preferably greater than 16 ml/g and 25 ml/g or less. That is, this monolithic intermediate basically has a continuous macropore structure, but since the opening (mesopore) which is the overlapping portion of one macropore and the other macropore is remarkably large, the framework constituting the monolithic structure has a structure that is as close as possible to the one-dimensional rod-like framework from the two-dimensional wall surface. When this is made to coexist in the polymerization system, a porous body having a co-continuous structure is formed by using the structure of the monolith intermediate as a mold. When the total pore volume exceeds 16 ml/g, it is possible to easily prevent the structure of the monolith obtained after polymerizing the vinyl monomer from changing from the co-continuous structure to the continuous macropore structure. In the meantime, when the total pore volume is 30 ml/g or less, it is possible to easily prevent the mechanical strength of the monolith obtained after polymerizing the vinyl monomer from being lowered and the anion exchange capacity per volume from being lowered. In order to bring the total pore volume of the monolithic intermediate into a specific range of B-type monolithic anion exchangers, the ratio of monomer to water may be approximately 1:20 to 1:40.

In the monolith intermediate, an average diameter of the openings (mesopores), which are overlapping portions of the macropores, is 5 to 100 μm in a dry state. When the average diameter of the openings is 5 μm or more in the dry state, it is possible to easily prevent the opening diameter of the monolith obtained after polymerizing the vinyl monomer from becoming small and the pressure loss at the time of fluid permeation from becoming large. In the meantime, when the average diameter is 100 μm or less, it is possible to easily prevent the opening diameter of the monolith obtained after polymerizing the vinyl monomer from becoming large, and it is easy to secure the contact between the water to be treated and the monolithic anion exchanger, and as a result, it is possible to easily prevent the hydrogen peroxide decomposition characteristic from deteriorating. The monolith intermediate preferably has a uniform structure in which the size of the macropores and the diameter of the openings are uniform, but is not limited to this, and may have non-uniform macropores that are larger than the size of the uniform macropores scattered in the uniform structure.

The B-type monolithic anion exchanger swells greatly, for example, 1.4 to 1.9 times as much as the monolith of the co-continuous structure because the anion exchange group is introduced into the monolith. In addition, even if the pore diameter increases due to swelling, the total pore volume does not change. Therefore, the B-type monolithic anion exchanger has a thick framework and therefore has high mechanical strength despite the remarkably large three-dimensionally continuous pore size. In addition, since the framework is thick, the anion exchange capacity per volume in a water-wetted state can be increased, and moreover, the water to be treated can be penetrated at a low pressure and a large flow rate for a long period of time.

Figure 2:
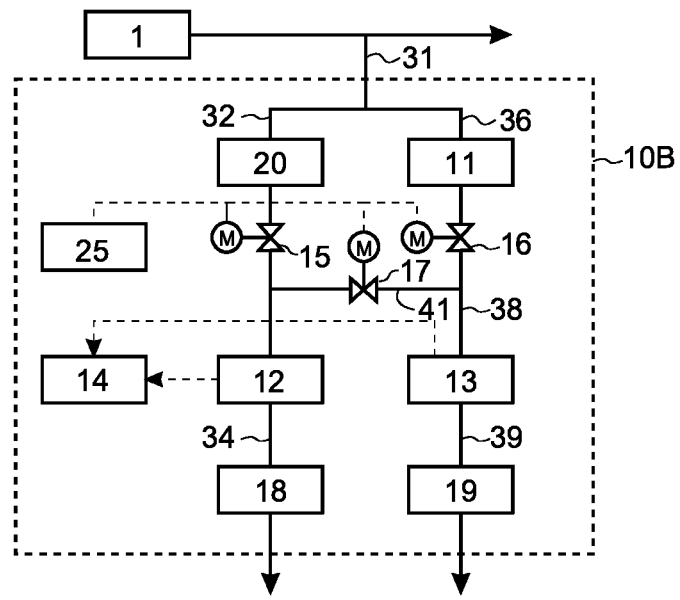
FIG. 2 is a configuration diagram of a hydrogen peroxide concentration measurement system according to another embodiment of the present invention.

Returning to FIG. 1, in an analysis pipe line for measuring the dissolved oxygen concentration of the sample water (hereinafter, referred to as the sample water pipe line) and an analysis pipe line for measuring the dissolved oxygen concentration of the treated water (hereinafter, referred to as the treated water pipe line), conditions such as a larger pressure loss and an increase in the number of joints are different as the treated water pipe line is equipped with the hydrogen peroxide decomposition device 11. As a result, there is a possibility that the measured values of the first dissolved oxygen analyzer 12 and the second dissolved oxygen analyzer 13 installed at the subsequent stage may fluctuate. Therefore, as in the hydrogen peroxide concentration measurement system 10B shown in FIG. 2, the condition adjustment unit 20 may be provided on the upstream side of the first on-off valve 15 of the pipe line 32 of the sample water pipe line. The condition adjustment unit 20 can be configured as a column (container) filled with a material (hereinafter, referred to as a condition adjustment material) that equalizes the water flow conditions of the sample water pipe line and the treated water pipe line, such as causing a pressure loss equivalent to that of the hydrogen peroxide decomposition device 11. The condition adjustment unit 20 may be any unit which does not have a function of generating oxygen, such as a hydrogen peroxide decomposition reaction, and is preferably one which is not dissolved by water and is excellent in durability, although it is not particularly limited. For example, if the hydrogen peroxide decomposition device 11 includes a column filled with a platinum group metal catalyst in which a platinum group metal is supported on a carrier, the condition adjustment unit 20 can be a column filled with only the carrier as a condition adjustment material. It should be noted that such a condition adjustment unit 20 is also applicable to the configurations of FIGS. 3 to 5 to be described later.

When a column filled with a material having a hydrogen peroxide decomposition capability is used as the hydrogen peroxide decomposition device 11, the flow rate of the water through the column is appropriately determined depending on various conditions such as the type of the filler and the hydrogen peroxide concentration of the sample water to be analyzed. When the flow rate is lowered, the contact time between the hydrogen peroxide and the filler increases, the decomposition rate of the hydrogen peroxide increases, and the generation rate of oxygen tends to increase. However, the effect of the increase of the dissolved oxygen concentration is apt to occur due to the permeation of oxygen in the atmosphere through the column and the pipe line system. On the other hand, if the flow rate is increased, the effect of the increase in the dissolved oxygen concentration due to the permeation of oxygen in the atmosphere becomes difficult to occur. However, there is a tendency that the contact time between hydrogen peroxide and the filler decreases, the decomposition amount of hydrogen peroxide decreases, the generation rate of oxygen decreases, and the analysis accuracy decreases.

A material of the column to be filled with the material having the hydrogen peroxide decomposing ability is not particularly limited, but it is preferable that the permeability of oxygen is low. Further, it is preferable that it is transparent so that the presence or absence of bubbles in the column can be confirmed at the time of starting up the system, and that it has excellent durability. Examples of such materials include acrylic resin, polyvinyl chloride, polycarbonate, and the like.

The dissolved oxygen contained in the sample water and the treated water is measured by the first dissolved oxygen analyzer 12 and the second dissolved oxygen analyzer 13 (measured value acquisition step). The two dissolved oxygen analyzers 12 and 13 can be constituted by a known dissolved oxygen analyzer.

The two dissolved oxygen analyzers 12 and 13 are not particularly limited, but are preferably of the same type and lot in order to reduce individual differences as much as possible.

The measured values of the two dissolved oxygen analyzers 12 and 13 are transmitted to the arithmetic unit 14, and the arithmetic unit 14 calculates the hydrogen peroxide concentration in the sample water based on a predetermined arithmetic expression.

The hydrogen peroxide concentration can be obtained from the dissolved oxygen concentration by the following calculation. That is, the difference between the dissolved oxygen concentration in the treated water and the sample water (a value obtained by subtracting the measured value of the first dissolved oxygen analyzer 12 from the measured value of the second dissolved oxygen analyzer 13) is derived from hydrogen peroxide in the water as shown in the Chemical Formula (1). Therefore, the concentration of hydrogen peroxide contained in the sample water can be calculated from the following equation based on the difference between the measured dissolved oxygen concentrations.

Assuming that the dissolved oxygen concentration value is DO, the difference $\Delta 1$ between the dissolved oxygen concentration values in the treated water and the sample water (this difference $\Delta 1$ obtained in the measured value acquisition step is also referred to as the "measured value") is (treated water DO–sample water DO), $$\text{Hydrogen peroxide concentration in sample water} = \Delta 1 \times (68/32) \quad (2)$$

Here, 68 is the molecular weight of hydrogen peroxide on the left side (twice because of two molecules), and 32 is the molecular weight of oxygen on the right side of the Chemical Formula (1). The unit of the left side is the same as the unit of DO of the right side.

Since the dissolved oxygen analyzer is adjusted so as to have the smallest error in a predetermined flow rate range, it is preferable to adjust the flow rate within that range. Therefore, it is preferable to provide a flow meter at the subsequent stage of the dissolved oxygen analyzer. As a result, the sample water and the treated water can be supplied to the hydrogen peroxide decomposition catalyst and the dissolved oxygen analyzer at appropriate flow rates.

Furthermore, it is preferable to provide a mechanism for indicating the flow rate and stabilizing the flow rate at an appropriate value. In FIG. 1, a flow rate stabilizing device (flow rate stabilizing means) 18 is provided in the downstream pipe line 34 of the first dissolved oxygen analyzer 12, and a flow rate stabilizing device (flow rate stabilizing means) 19 is provided in the downstream pipe line 39 of the second dissolved oxygen analyzer 13. The flow rate stabilizing means 18 and 19 are not particularly limited, but examples thereof include a combination of a flow meter and a valve capable of adjusting the flow rate. The flow rate stabilizing devices 18 and 19 are preferably provided downstream of the dissolved oxygen analyzer because oxygen may enter from the joints thereof. In addition, a well-known configuration such as an alarm device can be optionally added for a process control system. The sample water and the treated water whose dissolved oxygen concentration has been measured are drained after the flow rate measurement. Since the measurement reagent and the like are not added, the wastewater treatment is also easy.

It is desirable to calibrate and use the dissolved oxygen analyzer. Calibration of the dissolved oxygen analyzer is generally performed by atmospheric calibration when the sensor is exposed to the atmosphere and/or zero-point calibration with an aqueous solution in which a reducing agent such as sodium sulfite is excessively dissolved to remove the dissolved oxygen concentration. However, even when such a calibration is performed, in the measurement of the µg/L level, it is inevitable that a slight individual difference occurs in the dissolved oxygen analyzer. Particularly, in the case of measuring the dissolved oxygen concentration at the µg/L level by using two dissolved oxygen analyzers as in the present embodiment, the slight individual difference becomes more problematic.

Therefore, in the present embodiment, either the sample water or the treated water is simultaneously supplied to both of the two dissolved oxygen analyzers 12 and 13, the difference between the measured values of the two is obtained (correction value obtaining step) as a correction value that is used to correct the individual difference between the dissolved oxygen analyzers 12 and 13. The measured values of the two dissolved oxygen analyzers 12 and 13 are transmitted to the arithmetic unit 14, and the arithmetic unit 14 calculates the individual difference between the two dissolved oxygen analyzers 12 and 13 based on a predetermined arithmetic expression, and calculates the hydrogen peroxide concentration by correcting the individual difference. That is, when the measurement value of the first dissolved oxygen analyzer 12 (sample water measurement side) is A and the measurement value of the second dissolved oxygen analyzer 13 (treated water measurement side) is B when the sample water or treated water is passed through, the correction value (difference) Δ2 is:

$$\Delta 2 = B - A.$$

The hydrogen peroxide concentration corrected for individual differences is calculated by:

$$\text{Hydrogen peroxide concentration} = (\Delta 1 - \Delta 2) \times (68/32) \qquad (3)$$

As a result, it is possible to calculate a value with high accuracy by correcting the individual difference between the two dissolved oxygen analyzers.

In the case where either the sample water or the treated water is simultaneously supplied to both of the two dissolved oxygen analyzers to calculate the correction value, it is preferable that the two dissolved oxygen analyzers are supplied with the same flow rate. For this purpose, it is preferable to provide a flow rate stabilizing means for stabilizing the flow rate at an appropriate value in the downstream of the dissolved oxygen analyzer.

Next, the opening and closing control of the valve will be described.

In the configuration of FIG. 1, during the normal hydrogen peroxide concentration measurement (referred to as "measurement value acquisition mode"), the first on-off valve 15 is opened, the second on-off valve 16 is opened, and the connection valve 17 is closed. When the correction value is calculated, the first on-off valve 15 is opened, the second on-off valve 16 is closed, and the connection valve 17 is opened when the sample water is simultaneously introduced into both dissolved oxygen analyzers (referred to as "first correction value acquisition mode"). When the treated water is simultaneously introduced into both dissolved oxygen analyzers, the first on-off valve 15 is closed, the second on-off valve 16 is opened, and the connection valve 17 is opened (referred to as "second correction value acquisition mode"). Both the first correction value acquisition mode and the second correction value acquisition mode are "correction value acquisition mode". In FIG. 1, the opening and closing control of each valve is performed using the valve control device 25, but each valve may be opened and closed manually without using the valve control device 25. This also applies to other embodiments.

The flow direction through the connection valve 17 differs between the case where the sample water is introduced into both dissolved oxygen analyzers and the case where the treated water is introduced into both dissolved oxygen analyzers. Therefore, the connection valve 17 is not particularly limited, but it is preferable that the flow direction is not limited, such as a ball valve.

Figure 3:
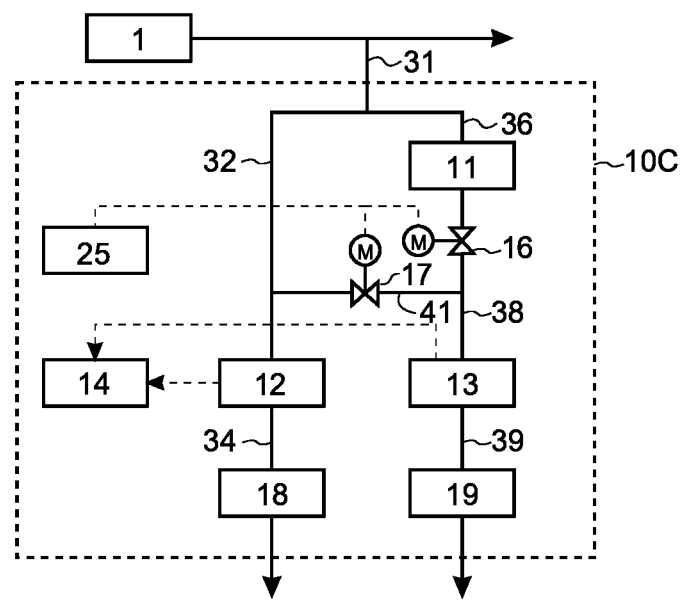
FIG. 3 is a configuration diagram of a hydrogen peroxide concentration measurement system according to another embodiment of the present invention.
Figure 4:
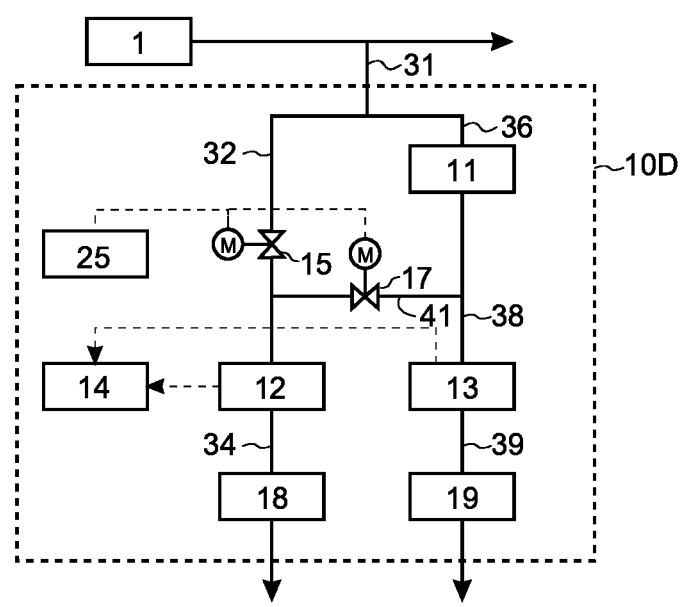
FIG. 4 is a configuration diagram of a hydrogen peroxide concentration measurement system according to another embodiment of the present invention.

When it is determined in advance to use either the sample water or the treated water, the configuration of FIG. 3 or FIG. 4 may be used. FIG. 3 shows a hydrogen peroxide concentration measurement system 10C in the case where the sample water is measured using two dissolved oxygen analyzers when calculating the correction value. In this system 10C, as compared with FIG. 1, the first on-off valve 15 is absent, and the valve 16 is used as a first on-off valve. FIG. 4 shows a hydrogen peroxide concentration measurement system 10D in the case where two dissolved oxygen analyzers are used to measure the treated water when calculating the correction value. Compared to FIG. 1, the system 10D does not have the second on-off valve 16 and includes only the first on-off valve 15. Otherwise, they are the same as in FIG. 1, and a detailed description thereof will be omitted.

In the configuration of FIG. 3, in the measurement value acquisition mode, the connection valve 17 is closed, and the first on-off valve 16 is opened. In the correction value acquisition mode, the connection valve 17 is opened, and the first on-off valve 16 is closed. In the configuration of FIG. 4, in the measurement value acquisition mode, the connection valve 17 is closed, and the first on-off valve 15 is opened. In the correction value acquisition mode, the connection valve 17 is opened, and the first on-off valve 15 is closed. In the configuration of FIG. 3 or FIG. 4, the number of valves can be reduced compared to the configuration of FIG. 1. As a result, the amount of oxygen entering the water from the valve can be reduced, and the maintenance of the valve can also be reduced.

Returning to FIG. 1, the timing of switching each valve between a state in which the first on-off valve 15 is opened and the second on-off valve 16 is opened and the connection valve 17 is closed at the time of normal hydrogen peroxide concentration measurement (measurement value acquisition mode), and a state in which the first on-off valve 15 is opened, the second on-off valve 16 is closed and the connection valve 17 is opened (correction value acquisition mode) at the time of introducing the sample water into both dissolved oxygen analyzers and calculating the correction value will be described.

First, at the time of switching from the normal hydrogen peroxide concentration measurement state (measurement value acquisition mode) to the state in which the sample water is introduced into both dissolved oxygen analyzers and the correction value is calculated (first correction value acquisition mode), the timing of switching the second on-off valve 16 from open to close and the timing of switching the connection valve 17 from close to open can be arbitrarily set and can be completely simultaneous, but it is preferable to switch the second on-off valve 16 from open to close after the completion of switching the connection valve 17 from close to open. This is because, if the connection valve 17 is switched from the closed state to the opened state after the second on-off valve 16 is switched from the opened state to the closed state, the flow rate to the second dissolved oxygen analyzer 13 is once interrupted, and there arises a problem that it takes time for the measured value to stabilize.

Next, in the case of switching from the state in which the sample water is introduced into both dissolved oxygen analyzers and the correction value is calculated (first correction value acquisition mode) to the normal hydrogen peroxide concentration measurement state (measurement value acquisition mode), it is preferable to switch the connection valve 17 from the open state to the closed state after the switching of the second on-off valve 16 from the closed state to the open state is completed for the same reason as described above.

Further, it is preferable that the switching of the first on-off valve 15 and the connection valve 17 at the time of switching between a normal hydrogen peroxide concentration measurement state (measurement value acquisition mode) and a state in which the treated water is introduced into both dissolved oxygen analyzers and the correction value is calculated (second correction value acquisition mode) is performed at the same timing as described above.

For the calculation of the correction value Δ2, it is preferable to obtain an average value of the measurement values for a certain period of time after the valve is switched and left for a certain period of time until the measured values are stable.

The timing at which the correction value Δ2 is obtained (the timing at which the correction value acquisition step is performed) can be set arbitrarily (regularly or irregularly), but it is preferable that the timing be between every day and every six months. At a frequency of one day or more, it is possible to easily prevent the mode from being switched to the mode for obtaining the correction value frequently and prolonging the time period during which the hydrogen peroxide concentration cannot be output. At a frequency of not more than six months, the calibration frequency of the sensor can be made moderate, and the reliability of the measured value can be easily prevented from becoming poor. In a period other than the period during which the correction value acquisition step is performed, it is preferable to continuously perform the measurement value acquisition step.

It is more preferable to use sample water as a target measurement water when obtaining the correction value Δ2. In this case, the dissolved oxygen concentration in the sample water is always output. That is, the dissolved oxygen concentration can be monitored even during the acquisition of the correction value Δ2.

Also, more reliable measurement values can be obtained by performing normal calibration of the dissolved oxygen analyzer (such as atmospheric calibration and/or zero-point calibration) as appropriate.

While the hydrogen peroxide concentration is calculated from Equation (3) at the time of normal hydrogen peroxide concentration measurement, it is possible to suppress the variation by taking a moving average of the values for a predetermined period of time.

Figure 5:
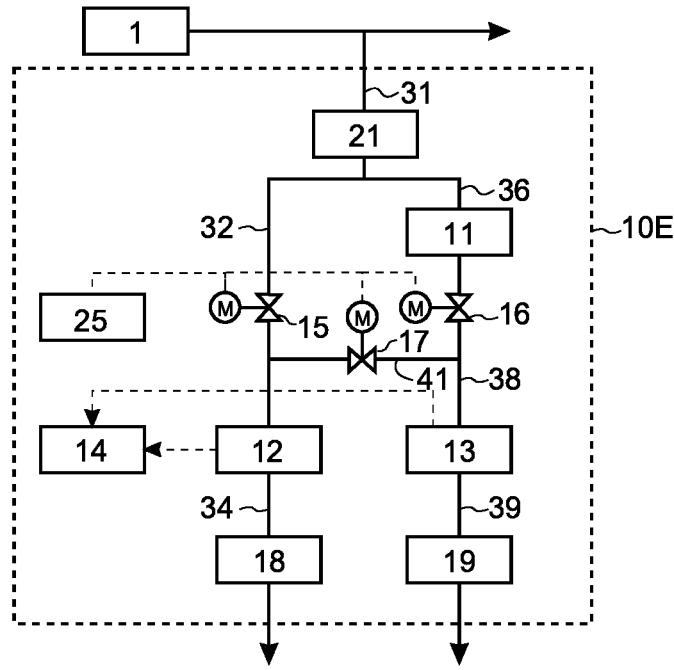
FIG. 5 is a configuration diagram of a hydrogen peroxide concentration measurement system according to another embodiment of the present invention.

As in a hydrogen peroxide concentration measuring system 10E shown in FIG. 5, a degassing device (degassing means) 21 may be provided in the pipe line 31 for collecting the sample water to degas the oxygen dissolved in the sample water. As the degassing device 21, for example, a membrane type degassing device or the like is used. The membrane type degassing device is an apparatus in which the water to be treated flows into one chamber partitioned by a gas separation membrane, and gas contained in the water to be treated is transferred to and removed from the other chamber through the gas separation membrane by depressurizing the other chamber. As the gas separation membrane, a membrane formed of a hydrophobic polymer membrane such as tetrafluoroethylene, silicone rubber, or the like in an appropriate shape such as a hollow fiber membrane is usually used. Such a degassing device is effective for measuring the hydrogen peroxide concentration with high accuracy when the dissolved oxygen concentration in the sample water is high or largely fluctuates. The degassing device 21 is also applicable to the configurations of FIGS. 2 to 4.

Depending on the hydrogen peroxide concentration (measurement range) in the sample water, for example, since the hydrogen peroxide concentration in pure water or ultrapure water system is several tens μg/L or less, it is suitable to degas (deoxidize) into the dissolved oxygen concentration of 100 μg/L or less, particularly preferably 10 μg/L or less, in order to lower the blank value. In addition, although the method of degassing is not particularly limited, the treatment by the membrane degassing device is preferable in that a compact and high-level degassing process can be performed. When the concentration of hydrogen peroxide in the sample water is high, or when analysis with high precision is not necessary, or when the concentration of dissolved oxygen in the sample water is originally low, it is not always necessary to install a degassing device.

It is preferable to use a material having a low gas permeability, such as stainless steel or nylon, for the pipe line used in the hydrogen peroxide concentration measuring system described above, in particular, for the pipe line from the sampling point where the sample water is introduced to the dissolved oxygen analyzer. These are preferable because they have a small oxygen transmittance and little elution of impurities.

Further, when a material of stainless steel is used for the pipe line of the hydrogen peroxide concentration measuring system, it is preferable to perform welding or bending without using as much as possible joints such as elbows or tees in the branch portion or the bent portion of the pipe line. The reason for this is that oxygen in the atmosphere can easily be prevented from permeating through joints and pipe line of fittings and dissolving into the sample water in a large amount to increase the dissolved oxygen concentration, and accurate measurement is easy.

In the embodiment described above, the sample water collected from the pipe line 31 was divided into the sample water pipe line and the treated water pipe line and measured, respectively. However, the sample water for the sample water pipe line and the sample water for the treated water pipe line may be collected independently (not shown). However, since there is a possibility that the conditions such as the dissolved oxygen concentration may differ when the sampling position is largely separated, it is preferable to branch and measure the sample water collected at one position.

Figure 7:
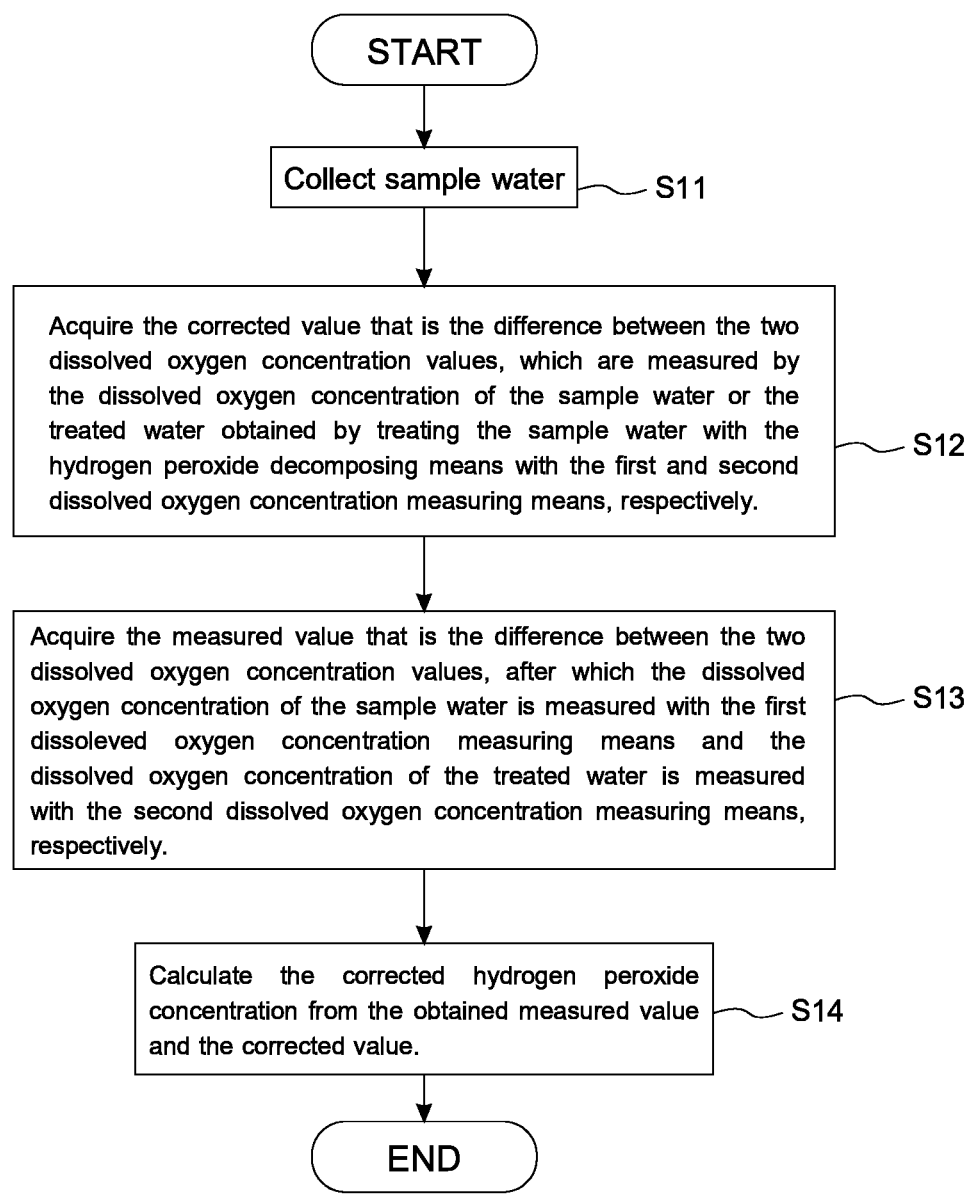
FIG. 7 is a flowchart of a hydrogen peroxide concentration measurement method according to an embodiment of the present invention.
Figure 8:
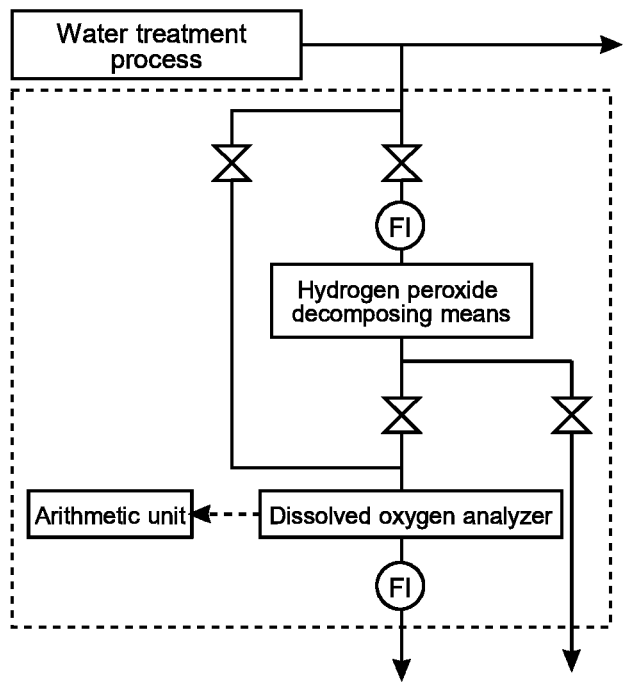
FIG. 8 is an example of a conventional hydrogen peroxide concentration measuring apparatus.
Figure 9:
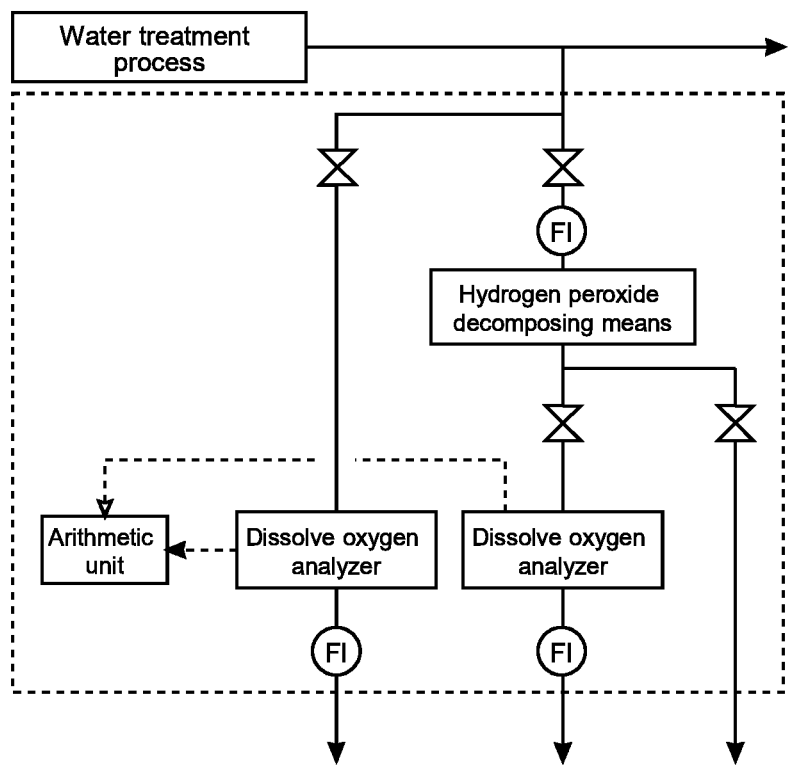
FIG. 9 is an example of a conventional hydrogen peroxide concentration measuring apparatus.

The measurement method of the hydrogen peroxide concentration described above will be explained with reference to FIG. 7. First, sample water is collected in step S11 of FIG. 7. Next, the dissolved oxygen concentration of the sample water or the treated water obtained by treating the sample water with the hydrogen peroxide decomposing means is measured by the first dissolved oxygen concentration measuring means and the second dissolved oxygen concentration measuring means, and the correction value that is the difference between the two dissolved oxygen concentration values is obtained in step S12. Next, the concentration of dissolved oxygen in the sample water is measured by the first dissolved oxygen concentration measuring means, and the concentration of dissolved oxygen in the treated water is measured by the second dissolved oxygen concentration measuring means to acquire the measured value that is the difference between the two dissolved oxygen concentration values in step S13. In step S14, the corrected hydrogen peroxide concentration is calculated from the last obtained measured value and the corrected value. Step S12 is performed as appropriate, and step S13 and step S14 are performed simultaneously in other normal cases. In other words, the hydrogen peroxide concentration is calculated by immediately correcting the measured value obtained continuously at the normal time with the correction value.

According to the above embodiment, the hydrogen peroxide in the sample water can be quantified continuously and with high accuracy. In addition, since the measurement of the hydrogen peroxide concentration in the sample water can be automated, it is possible to realize a hydrogen peroxide analysis system and a hydrogen peroxide analysis method which are particularly suitable for a pure water or an ultrapure water production facility in which human intervention is to be avoided as much as possible. Further, even when a fluctuation (sudden change) occurs in the dissolved oxygen concentration contained in the sample water, the fluctuation does not affect the measurement value of the hydrogen peroxide concentration, and the hydrogen peroxide concentration can be accurately measured.

EXAMPLES

Hereinafter, specific examples of the present invention will be described as Examples.

Example 1

Sample water of four conditions having different hydrogen peroxide concentrations was introduced into the hydrogen peroxide concentration measurement system 10E shown in FIG. 5, and the hydrogen peroxide concentration was measured.

Immediately before the measurement of the hydrogen peroxide concentration under each condition, the sample water was simultaneously passed through both the first dissolved oxygen analyzer 12 and the second dissolved oxygen analyzer 13 for one hour, and the correction value Δ2 for the calculation of the hydrogen peroxide concentration was calculated by using the average value of the difference between the measured values in the latter half of 30 minutes. The hydrogen peroxide concentration was then calculated according to Equation (3).

After the calculation of the correction value Δ2, the dissolved oxygen concentration contained in the sample water and the treated water was measured by two dissolved oxygen analyzers at the same time, and the average value for 3 minutes after the measured value stabilized was used as the measured value of the hydrogen peroxide concentration in the sample water. As a reference value, the concentration of hydrogen peroxide in the sample water was analyzed by the phenolphthalein colorimetric method described in Patent Document 3.

From the above, the hydrogen peroxide concentration measurement result (Example 1) of the sample water according to the present invention and the hydrogen peroxide concentration measurement result (reference value) of the sample water by the phenolphthalein colorimetry method were obtained. The results are given in Table 1. When the measurement results of Example 1 and the reference values were compared, the difference was 0.5 µg/L or less in all four conditions in which the hydrogen peroxide concentration of the sample water was different.

TABLE 1

| | $H_2O_2$ Concentration (µg/L) | | |
|---|---|---|---|
| Condition | Example 1 | Reference Value | Difference |
| 1 | 0.1 | 0 | 0.1 |
| 2 | 1.0 | 0.9 | 0.1 |
| 3 | 5.5 | 5.1 | 0.4 |
| 4 | 10.8 | 10.8 | 0 |

Comparative Example 1

Sample water of four conditions having different hydrogen peroxide concentrations was introduced into the hydrogen peroxide concentration measurement system 10E shown in FIG. 5, and the hydrogen peroxide concentration was measured.

Immediately before measuring the hydrogen peroxide concentration under each condition, two-point calibration was performed, namely, air calibration in the case where both the sensors of the first dissolved oxygen analyzer 12 and the second dissolved oxygen analyzer 13 were exposed to the atmosphere, and zero-point calibration in an aqueous solution in which a reducing agent such as sodium sulfite was excessively dissolved to remove the dissolved oxygen concentration.

Then, the dissolved oxygen concentrations contained in the sample water and the treated water were measured simultaneously by the calibrated first dissolved oxygen analyzer 12 and the calibrated second dissolved oxygen analyzer 13, respectively, and the hydrogen peroxide concentration was calculated from the measured dissolved oxygen concentration using the Equation (2).

The dissolved oxygen concentration contained in the sample water and the treated water was measured simultaneously by the first dissolved oxygen analyzer 12 and the second dissolved oxygen analyzer 13, respectively, and the average value for 3 minutes after the measured value stabilized was used as the measured value of the hydrogen peroxide concentration of the sample water. The concentration of hydrogen peroxide in the sample water was analyzed by the phenolphthalein colorimetric method described in Patent Document 3.

From the above, without applying the present invention, the hydrogen peroxide concentration of the sample water was measured (Comparative Example 1) and the hydrogen peroxide concentration measurement result (reference value) of the sample water by the phenolphthalein colorimetric method described in Patent Document 3 were obtained as a result of measuring the hydrogen peroxide concentration of the sample water by performing only the usual two-point calibration of the two dissolved oxygen analyzers. The results are given in Table 2.

TABLE 2

| | $H_2O_2$ Concentration (µg/L) | | |
|---|---|---|---|
| Condition | Comparative Example 1 | Reference Value | Difference |
| 1 | −0.8 | 0 | 0.8 |
| 2 | 0.2 | 0.9 | 0.7 |
| 3 | 4.5 | 5.1 | 0.6 |
| 4 | 10.1 | 10.8 | 0.7 |

Comparing the measurement results of Comparative Example 1 and the reference values, a difference of 0.5 µg/L or more was confirmed in all four conditions in which the hydrogen peroxide concentration of the sample water was different. In addition, since the correction value Δ2 was not taken into consideration, it was also confirmed that the measurement result of Comparative Example 1 exhibited a negative value in Condition 1.

Example 2

Ultra-pure water containing hydrogen peroxide was introduced as sample water into the hydrogen peroxide concentration measurement system 10E shown in FIG. 5, and the hydrogen peroxide concentration was measured Immediately before the hydrogen peroxide concentration was measured, the sample water was simultaneously supplied to both the first dissolved oxygen analyzer 12 and the second dissolved oxygen analyzer 13 for one hour, and the correction value Δ2 of the hydrogen peroxide concentration calculation was calculated by using the average value of the difference between the measured values in the latter half 30 minutes. The hydrogen peroxide concentration was then calculated according to Equation (3). The results are shown in FIG. 6.

Figure 6:
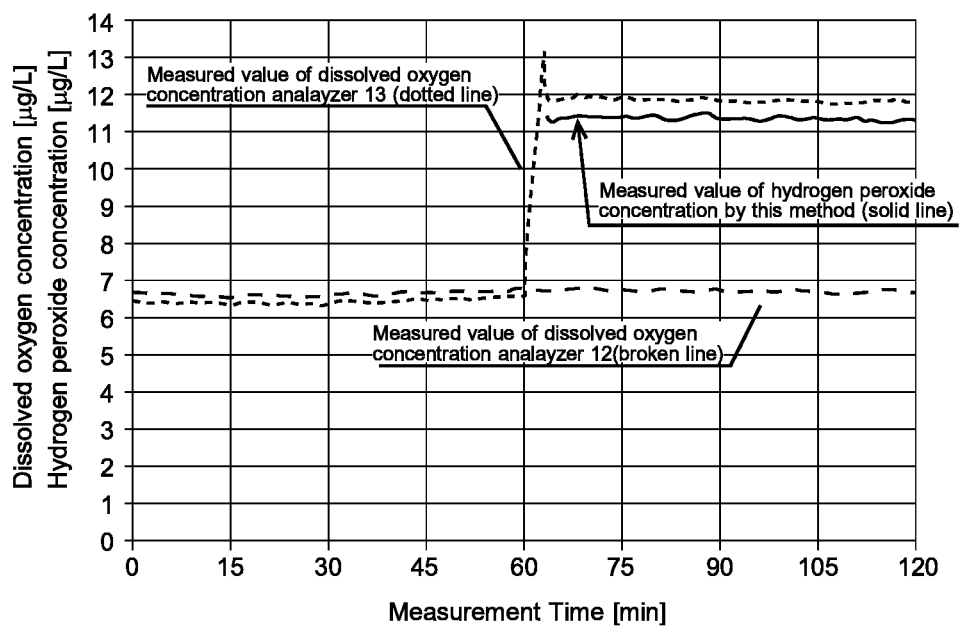
FIG. 6 is a graph showing a measurement result of a hydrogen peroxide concentration according to an embodiment of the present invention.

As is obvious from FIG. 6, since the dissolved oxygen concentration of the sample water is always measured by the first dissolved oxygen analyzer 12, the dissolved oxygen concentration (broken pipe line in FIG. 6) of the sample water can be continuously measured (monitored) without interruption.

DESCRIPTION OF REFERENCES

1 Water treatment process
10A-10E Hydrogen Peroxide Concentration Measurement System
11 Hydrogen peroxide decomposition device (hydrogen peroxide decomposition means)
12 First dissolved oxygen analyzer (first dissolved oxygen concentration measuring means)
13 Second dissolved oxygen analyzer (second dissolved oxygen concentration measuring means)
14 Arithmetic unit (calculation means)
15 First on-off valve
16 Second on-off valve (or first on-off valve)
17 Connection valve
18,19 Flow rate stabilizing device (flow rate stabilizing means)
20 Condition adjustment unit
21 Degassing device (degassing means)
25 Valve control device (valve control means)
31 Sample water sampling pipe line (sample water sampling means)
32 First pipe line
38 Second pipe line
41 Connection pipe line

The invention claimed is:

1. A method for measuring a concentration of hydrogen peroxide in sample water collected from a predetermined position in a water treatment process, the method comprises:
collecting the sample water,
obtaining a corrected value that is a difference between two dissolved oxygen concentration values, the two dissolved oxygen concentration values being measured by using a first dissolved oxygen concentration measuring analyzer and a second dissolved oxygen concentration measuring analyzer, respectively, for the sample water or a treated water obtained by treating the sample water with a hydrogen peroxide decomposing device,
obtaining a measured value that is a difference between two dissolved oxygen concentration values, the two dissolved oxygen concentration values being obtained by measuring a concentration of the dissolved oxygen in the sample water by the first dissolved oxygen concentration measuring analyzer, and measuring a concentration of the dissolved oxygen in the treated water by the second dissolved oxygen concentration measuring analyzer, and calculating a corrected concentration of hydrogen peroxide in the sample water by the following equation:

$$(\Delta 1 - \Delta 2) \times (68/32)$$

wherein Δ1 is the measured value obtained in the measured value obtaining, and Δ2 is the corrected value obtained in the corrected value obtaining.

2. The method for measuring a concentration of hydrogen peroxide according to claim 1, wherein the corrected value obtaining measures the dissolved oxygen concentration of the sample water by the first dissolved oxygen concentration measuring analyzer and the second dissolved oxygen concentration measuring analyzer.

3. The method for measuring a concentration of hydrogen peroxide according to claim 1, wherein the collecting includes degassing the collected sample water.

4. A hydrogen peroxide concentration measurement system for measuring a concentration of hydrogen peroxide in sample water collected from a predetermined position in a water treatment process, the system comprises:
a sample water collector collecting the sample water,
a route introducing the collected sample water into a first dissolved oxygen concentration measuring analyzer through a first pipe line to measure a concentration of dissolved oxygen,
a route introducing the collected sample water into a hydrogen peroxide decomposition device to obtain a treated water subjected to a decomposition treatment of the hydrogen peroxide, and introducing the treated water into a second dissolved oxygen concentration measuring analyzer through a second pipe line to measure the dissolved oxygen concentration in the treated water,
a connection pipe line connecting the first pipe line and the second pipe line,
a first on-off valve disposed on an upstream side of a branch position in at least one of the first pipe line and the second pipe line with the connection pipe line,
a connection valve disposed in the connection pipe line,
a valve controller for controlling an opening and a closing of the first on-off valve and the connection valve, and
a calculator calculating a corrected concentration of hydrogen peroxide in the sample water from the following equation:

$$(\Delta 1 - \Delta 2) \times (68/32)$$

by setting a measured value measured in a measured value acquisition mode as Δ1, and setting a corrected value acquired in a corrected value acquisition mode as Δ2,
wherein the measured value is a difference between a dissolved oxygen concentration value of the sample water measured by the first dissolved oxygen concentration measuring analyzer and a dissolved oxygen concentration value of the treated water measured by the second dissolved oxygen concentration measuring analyzer, and the corrected value is a difference between the dissolved oxygen concentration values of the sample water or the treated water measured by the first and second dissolved oxygen concentration measuring analyzers.

5. The hydrogen peroxide concentration measurement system according to claim 4, wherein
the first pipe line or the second pipe line is provided with the first on-off valve,
the valve controller is controllable to establish the measured value acquisition mode in which the connection valve is closed and the first on-off valve is opened, and the corrected value acquisition mode in which the connection valve is opened and the first on-off valve is closed, and the calculator calculates a corrected hydrogen peroxide concentration from the measured value which is a difference between the dissolved oxygen concentration values measured by the first and second dissolved oxygen concentration measuring analyzers in the measured value acquisition mode and the corrected value which is a difference between the dissolved oxygen concentration values measured by the first and second dissolved oxygen concentration measuring analyzers in the corrected value acquisition mode.

6. The hydrogen peroxide concentration measurement system according to claim 4, wherein the first pipe line is provided with a first on-off valve, and the second pipe line is provided with a second on-off valve, the second on-off valve is controllable with the valve controller, and the valve controller is controllable to establish the measured value acquisition mode in which the connection valve is closed and both first and second on-off valves are opened, and the corrected value acquisition mode in which the connection valve is opened, one of the first and second on-off valves is opened and the other is closed, and the calculator calculates a corrected hydrogen peroxide concentration from the measured value which is a difference between the dissolved oxygen concentration values measured by the first and second dissolved oxygen concentration measuring analyzers in the measured value acquisition mode and the corrected value which is a difference between the dissolved oxygen concentration values measured by the first and second dissolved oxygen concentration measuring analyzers in the corrected value acquisition mode.

7. The hydrogen peroxide concentration measuring system according to claim 4, wherein the hydrogen peroxide decomposition device is a column filled with a platinum group metal catalyst in which a platinum group metal is supported on a carrier.

8. The hydrogen peroxide concentration measuring system according to claim 7, further comprising a column filled with only the carrier upstream of a branch portion of the first pipe line with the connection pipe line.

9. The hydrogen peroxide concentration measuring system according to claim 4, further comprising a flow rate stabilizer downstream of the first dissolved oxygen concentration measuring analyzer and the second dissolved oxygen concentration measuring analyzer, respectively.

10. The hydrogen peroxide concentration measurement system according to claim 4, wherein the sample water collector comprises a degassing device.

* * * * *